(12) United States Patent
Doyle et al.

(10) Patent No.: US 6,194,163 B1
(45) Date of Patent: Feb. 27, 2001

(54) METHOD FOR THE QUANTITATIVE MEASUREMENT OF HUMAN ACUTE PHASE SERUM AMYLOID A PROTEIN; RECOMBINANT PROTEIN; SPECIFIC ANTIBODY

(75) Inventors: John Martin Doyle, Deansgrange; Hazel Audrey Hobson, Arklow; Alexander Steven Whitehead, Delgany, all of (IE)

(73) Assignee: The Provost, Fellows and Scholars of the College of the Holy and Undivided Trinity of Queen Elizabeth Near Dublin, Dublin (IE)

( * ) Notice: Subject to any disclaimer, the term of this patent is extended or adjusted under 35 U.S.C. 154(b) by 0 days.

(21) Appl. No.: 08/983,475

(22) PCT Filed: Jul. 19, 1996

(86) PCT No.: PCT/IE96/00042

§ 371 Date: Mar. 23, 1998

§ 102(e) Date: Mar. 23, 1998

(87) PCT Pub. No.: WO97/04317

PCT Pub. Date: Feb. 6, 1997

(30) Foreign Application Priority Data

Jul. 21, 1995 (IE) .................................................. S950553

(51) Int. Cl.[7] .................................................. G01N 33/53
(52) U.S. Cl. .................. 435/7.92; 435/961; 435/962; 435/975; 435/69.6; 436/518; 436/71; 436/808; 530/388.25; 530/389.3
(58) Field of Search .................................. 435/7.92, 961, 435/962, 975, 69.6; 436/518, 71, 808; 530/388.25, 389.3

(56) References Cited

U.S. PATENT DOCUMENTS 4,755,380 * 7/1988 Grubb et al. .......................... 530/428
4,782,014 * 11/1988 Serban et al. ......................... 435/7.1
5,126,240 * 6/1992 Curtiss ................................ 435/7.94
5,290,686 * 3/1994 Kendal et al. ....................... 435/69.1

OTHER PUBLICATIONS

Raynes et al. 1991. Scand. J. Immunol. 33:657–666.*
Betts et al. 1991. Scand. J. Immunol. 34:471–482.*
Steinmetz et al. 1990. Electrophoresis. 11(8):627–630.*

Martin–Tino Casi et al., "A rapid enzyme–linked immunosorbent assay for serum amyloid A using sequence specific antibodies," Annals of Clinical Biochemistry, 30(3) 278–286, May 1993.*

Barbara Kluve–Beckerman et al., "Recombinant murine serum amyloid A from baculovirus–infected insect cells: purification and characterization", Biochimica et Biophysica Acta, 1182:303–310, 1993.*

Barbara Kluve–Beckerman et al., "Differential plasma clearance of murine acute–phase serum amyloid A proteins SAA1 and SAA2," Biochemical Journal, 322(part 2):663–669, Mar. 1993.*

Christine C. McCormack et al., "Generation of soluble recombinant human acute phase serum amyloid A2 (A–SAA2) protein and its use in development of a A–SAA specific ELISA," Journal of Immunological Methods, 198(1):101–110, Oct. 1996.*

Y.S. Taktak et al., "A solid phase enzyme immunoassay for serum amyloid A (SAA) protein," Journal of Immunological Methods, 136:11–16, 1991.*

Toshiyuki Yamada et al., "Fibril formation from recombinant human serum amyloid A," Biochimica et al Biophysica Acta, 1226:323–329, 1994.*

* cited by examiner

Primary Examiner—Christopher L. Chin
Assistant Examiner—Jennifer Graser
(74) Attorney, Agent, or Firm—Birch, Stewart, Kolasch & Birch, LLP

(57) ABSTRACT

The present invention is drawn to a method for the quantitative determination of human acute phase serum amyloid A protein (A-SAA) comprising contacting a sample of a biological fluid with antibody specific for A-SAA, the sample being reacted with an organic solvent prior to or simultaneous with antibody contact. The organic solvent is suitably a C1 or C4 alcohol and the antibody can be used on the solid phase and as a component of the detection system of an enzyme linked immunosorbant assay. The method provides a sensitive and reliable measure of A-SAA and inflammatory status which can be used for the diagnosis and clinical management of both acute and chronic inflammatory conditions.

14 Claims, 7 Drawing Sheets

SEQUENCE LISTING

<160> NUMBER OF SEQ ID NOS: 3

<210> SEQ ID NO 1
<211> LENGTH: 29
<212> TYPE: DNA
<213> ORGANISM: Homo sapiens

<400> SEQUENCE: 1
cgggatccgg gcgaagcttc ttttcgttc                                    29

<210> SEQ ID NO 2
<211> LENGTH: 27
<212> TYPE: DNA
<213> ORGANISM: Homo sapiens

```
-continued

<400> SEQUENCE: 2
cggaattcag tatttctcag gcaggcc                                27

<210> SEQ ID NO 3
<211> LENGTH: 19
<212> TYPE: PRT
<213> ORGANISM: Homo sapiens

<400> SEQUENCE: 3

Gly Ser Gly Arg Ser Phe Phe Ser Phe Leu Gly Glu Ala Phe Asp Gly
 1               5                  10                  15

Ala Arg Asp
```

METHOD FOR THE QUANTITATIVE MEASUREMENT OF HUMAN ACUTE PHASE SERUM AMYLOID A PROTEIN; RECOMBINANT PROTEIN; SPECIFIC ANTIBODY

This application is the national phase under 35 U.S.C. §371 of prior PCT International Application No. PCT/IE 96/00042 which has an International filing date of Jul. 19, 1996 which designated the United States of America, the entire contents of which are hereby incorporated by reference.

TECHNICAL FIELD

This invention relates to a method for the quantitative determination of human acute phase serum amyloid A protein (A-SAA) which distinguishes between the A-SAA and constitutive (C-SAA) forms of SAA.

BACKGROUND ART

The mammalian acute phase response is the first line of systemic defence elicited by stimuli such as infection, trauma, myocardial infarction, neoplasms, and surgery. It is initiated and maintained by a large number of pro-inflammatory mediators including cytokines, glucocorticosteroids and anaphylatoxins and involves a wide range of complex physiological changes including elevated circulating concentrations of hepatically synthesised acute phase reactants (APRs). In man, this latter class includes the "major" APRs, serum amyloid A (SAA) and C-reactive protein (CRP) (reviewed by Steel, D. M. and Whitehead, A. S. (1994) Immunol. Today (England) 15, 81).

The human SAA gene family is comprised of four known genes that have been localised to the short arm of chromosome 11p15.1. The SAA1 and SAA2 genes specify the two acute phase SAA proteins A-SAA1 and A-SAA2 respectively which are both 104 amino acid, 12.5 kDa proteins that share 93% amino acid sequence identity. A number of allelic forms have been identified by amino acid sequence analysis of A-SAA isolated from plasma. The A-SAA1 protein has three allelic forms whereas the A-SAA2 protein has two. A third gene SAA3 which shows 71% nucleotide identity with SAA1 and SAA2 is a pseudogene. Constitutive SAA (C-SAA) is the third expressed SAA family member and is the product of the SAA4 gene. C-SAA levels characteristically do not increase as a result of inflammation and exist in serum at concentrations between 80–140 mg/L (Yamada, T. et al. (1994) Int. J. Exp. Clin. Invest. 1, 114). C-SAA differs from A-SAA with respect to peptide length, being eight amino acids longer, and shares only 55% identity with A-SAAs. Additionally, C-SAA may be post-translationally modified by glycosylation at a single site. In common with the A-SAAs, C-SAA rapidly associates with high density lipoprotein (HDL3) when released into the circulation.

Circulating concentrations of A-SAA can increase up to 1000 mg/L within 24–48 hours of an acute stimulus (Marhaug, G. (1983); Scand. J. Immunol. 18, 329) indicating an important protective role for these proteins; however, no definitive function has been demonstrated for the A-SAA proteins. Recent studies variously suggest that A-SAA has chemoattractant activity, may play a role in lipid metabolism and immunosuppression and may inhibit the oxidative burst in neutrophils.

During chronic inflammation A-SAA levels remain significantly elevated reflecting the continued persistence of underlying pathological inflammatory processes that can contribute to long term tissue damage. An occasional consequence of chronic inflammation is reactive secondary amyloidosis, a progressive fatal condition in which amyloid A protein (AA), a cleavage product of A-SAA, is the major component of insoluble fibrous deposits that accumulate in major organs. The sustained elevation of A-SAA in chronic inflammatory conditions suggests that A-SAA is an important indicator of disease status. However, the measurement of A-SAA concentration has not been used for routine clinical diagnosis and clinical management, due in part to the difficulty in raising specific antisera against human A-SAA (Pepys, M. B. et al. (1984); British Medical Journal 288, 859).

Several methods, however, have been reported for the measurement of SAA levels: these include (i) radioimmunoassays and single radial immunodiffusion procedures (Chambers, R. E. and Whicher, J. T. (1983); J. Immunol. Methods 59, 95; Marhaug, G. (1983) supra; Taktak, Y. S. and Lee, M. A. (1991); J. Immunol. Methods 136, 11); (ii) ELISA based assays (Zuckerman, S. H. and Suprenant, Y. M.(1986); J. Immunol. Methods 92, 3743; Dubois, D. Y. and Malmendier, C. L. (1988); J. Immunol. Methods 112, 71–75; Sipe, J. D. et al. (1989); J. Immunol. Methods 125, 125–135; Yamada, T. et al. (1989); Clin. Chim. Acta 179, 169–176; Tino-Casl, M. and Grubb, A. (1993); Arm. Clin. Biochem 30, 278–286); (iii) nephelometric methods (Vermeer, H. et al. (1990); Clin. Chem 36, 1192; Yamada, T. et al. (1993); Ann. Clin. Biochem. 30, 72–76); (iv) an electrophoretic procedure (Godenir, N. L. et al. (1985); J. Immunol. Methods 83, 217); (v) an immunochemiluminescence procedure (Hachem, H. et al. (1991); Clin. Biochem 24, 143–147); (vi) an automated method based on a monoclonal-polyclonal antibody solid phase enzymeimmunoassay (Wilkins, J. W. et al. (1994); Clin. Chem 40(7), 1284–1290); and (vii) time-resolved fluorometric immunoassay (Malle, E., et al. (1995); J. Immunol. Methods 182, 131). As SAA in serum exists as one of the apolipoproteins associated with HDL3 particles many of these methods require denaturation of the serum samples (in an effort to eliminate the masking effect previously observed to be a problem in the accurate quantification of SAA) prior to carrying out the assay. Many assays previously reported have either measured total SAA or have been based on anti-sera raised against total SAA and have not been documented as being able to distinguish between the A-SAA and C-SAA proteins. Furthermore, many of these assays require an overnight incubation.

Problems have been encountered obtaining a soluble purified native A-SAA: purification of A-SAA protein from large volumes of blood is characterised by poor yields (Godenir, N. L. et al. (1985) supra), limited solubility (Bausserman, L. L. et al. (1983); J. Biol. Chem. 258, 10681) and the heterogeneous nature of the A-SAA recovered. In addition, A-SAA purified from serum may contain trace amounts of other serum components thereby potentially compromising studies of A-SAA function that involve sensitive bioassays.

There is a need for a method which provides a sensitive and reliable measure of A-SAA and inflammatory status which can be used for the diagnosis and clinical management of both acute and chronic inflammatory conditions.

WO 91/05874 is mainly concerned with total plasma protein immobilisation onto solid phases (e.g., polyvinyl chloride microtitre plates) and subsequent detection of said plasma proteins (e.g., SAA) using relevant antisera. The authors use inorganic salts and elevated temperatures as a means of promoting plasma protein adherence to the solid support. Reference is made to antigen capture ELISAs following specimen delipidation but this technique was found not to accurately and reproducibly facilitate detection of Serum Amyloid A. It is stated that antigen capture ELISAs do not provide the sensitivity required for clinically relevant measurements of SAA.

JP-A-63 0 44 895 refers to the generation of a monoclonal antibody, using a synthetic peptide, to a specific region to Serum Amyloid A protein which is proposed to have a potential utility in the diagnosis of secondary amyloidosis.

Biochemistry (1972), 11, 2934–2938 describes the primary sequence of a primate (Macaca mulatta) amyloid A protein and is concerned with the putative role of amyloid A in amyloidosis. No reference is made to the generation of antisera against the protein. While a fairly high degree of sequence homology is observed with the human activatable form of Serum Amyloid A it is unclear as to whether both proteins perform the same in vivo role in the two different species (Homo sapiens and Macaca mulatta).

Chemical Abstracts Vol. 125, No. 15 relates to the detection of Serum Amyloid A using antisera raised again the protein purified from human serum. The protein fraction purified from serum cannot be guaranteed to be free of the constitutive form and therefore cross-reactivity in any resultant ELISA test is a distinct possibility.

DISCLOSURE OF INVENTION

The invention provides a method for the quantitative determination of human acute phase serum amyloid A protein (A-SAA), which comprises contacting a sample of a biological fluid with antibody specific for A-SAA, said sample being reacted with an organic solvent prior to or simultaneous with antibody contact and said antigen which is used to raise the anti-A-SAA being recombinant A-SAA.

By biological fluid herein is meant body fluids such as plasma, serum, synovial fluid, urine and bile, more especially plasma and serum, a perfusate, tissue support media or cell/tissue culture media.

The biological fluid can be diluted.

Preferably, the antigen used to raise the anti-A-SAA is recombinant A-SAA.

Recombinant protein technology offers a means of generating a reliable, renewable, homogeneous source of A-SAA.

As stated above, the antigen used to raise the anti-A-SAA is recombinant A-SAA2.

No other immunoassay has been reported which utilises antibodies raised against recombinant A-SAA2.

The production of recombinant human A-SAA2 in *E.coli* as a GST (glutathione S-transferase) fusion protein using the pGEX expression system (Smith, D. B. and Johnson, K. S. (1988); Gene 67, 447) is described in Example 1. Expression of A-SAA2 in this system permits the recovery of soluble recombinant A-SAA2 protein following thrombin cleavage of the fusion protein when used in the presence of a mild non-ionic detergent as hereinafter described.

Preferably, the organic solvent is a polar organic solvent.

More especially, the organic solvent is a $C_1$–$C_4$ alcohol.

The organic solvent can include an amount of a $C_1$–$C_4$ ether.

Preferably, the organic solvent is used in an amount of 10–50% v/v of the sample diluent.

Most preferably, the organic solvent is used in an amount of 20–30% v/v of the sample diluent.

In a preferred embodiment, the antibody is used on the solid phase and as a component of the detection system of an enzyme linked immunosorbant assay (ELISA).

Antibodies raised against recombinant A-SAA2 were found to be specific for the A-SAAs and were used to develop a sandwich ELISA to quantify A-SAA levels in serum, as hereinafter described.

The ELISA described herein has a high sensitivity and can detect A-SAA concentrations of 5 µg/L in human serum and tissue culture media.

The invention also provides a test kit or pack for carrying out the method according to the invention.

The invention also provides substantially pure recombinant A-SAA2.

Further the invention provides antibodies specific for A-SAA1 and A-SAA2, more especially IgG class antibody, most especially polyclonal IgG.

The invention provides antibodies specific for the acute phase SAAs, A-SAA1 and A-SAA2, which show no cross-reactivity with the constitutively expressed SAA, namely C-SAA or other acute phase protein.

MODES FOR CARRYING OUT THE INVENTION

The invention will be further illustrated by the following Examples.

EXAMPLE 1

Construction of the A-SAA2 Protein Expression Vector

The coding region of A-SAA2 was amplified from the A-SAA2 cDNA clone by the polymerase chain reaction (PCR) with the concomitant introduction of sequence specifying an additional glycine residue and a BamHI restriction site at the 5' end (oligonucleotide primer sequence 5'-CGGGATCCGGGCGAAGCTTCTTTT CGTTC-3' (SEQ ID NO.1)) and an EcoRI site at the 3' end (oligonucleotide primer sequence 5'-CGGAATTCAGTATTTCTAGGCGGCC-3' (SEQ ID NO.2)). The PCR product was digested with BamHI and EcoRI, gel purified, and ligated into the Glutathione S-Transferase (GST) fusion protein expression vector pGEX-2T (Pharmacia Fine Chemicals, Milton Keynes, U.K.). The A-SAA2 coding region was inserted in frame into the pGEX-2T vector to produce a construct in which A-SAA2 expression was under the control of the isopropyl β-D-thiogalactosidase (IPTG) inducible tac promoter and GST ribosome binding site. DNA sequence analysis of the resulting pGEX-(A-SAA2) confirmed that it carried the entire unmodified A-SAA2 coding region positioned downstream of the GST coding region with no mutations resulting from the PCR process.

EXAMPLE 2

Induction of E. coli Cultures for High Level Expression of Recombinant A-SAA2 Protein Plasmid pGEX-(A-SAA2) was transformed into the E. coli expression strain NM554. Transformants were isolated and grown overnight at 37° C. Overnight cultures were diluted 1/100 in Luria broth containing 100 μg/ml ampicillin (Boehringer Mannheim, East Sussex, U.K.) and grown to an $OD_{600}$ value of 1.0. Expression of recombinant fusion protein was induced in culture with 0.1 mM isopropyl β-D-thiogalactosidase (IPTG: Sigma, Dorset, U.K.) for 5 h at 37° C. Cultures were centrifuged at 5000×g for 10 min at 4° C. Upon induction a 38.5 kDa GST-(A-SAA2) fusion protein was produced (see FIG. 1, lane 4) constituting approximately 5% of the total cellular protein.

Figure 1:
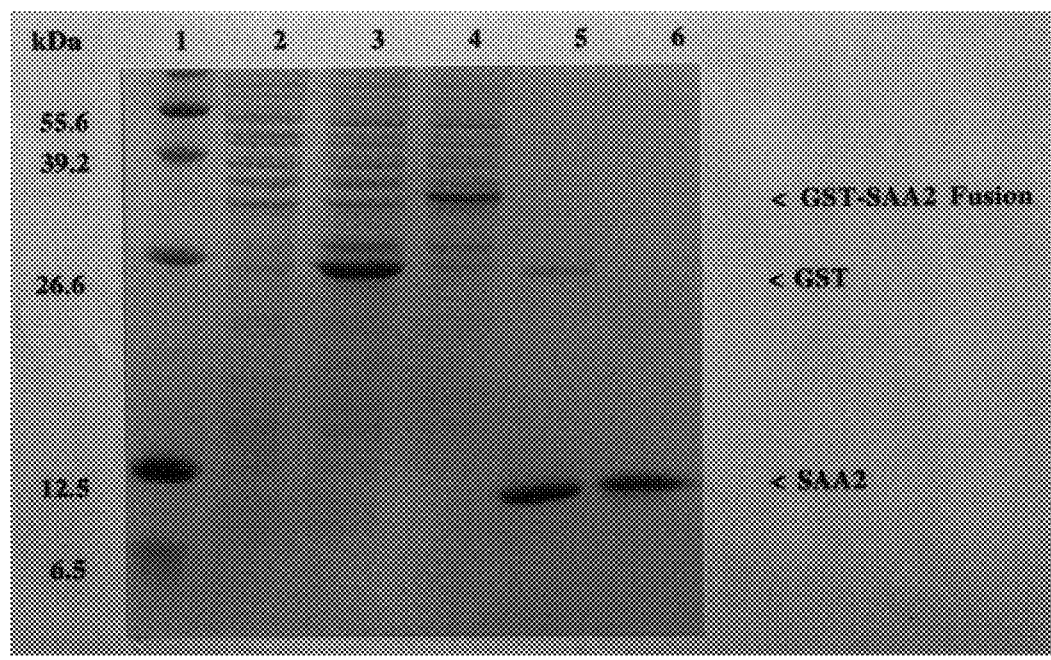
FIG. 1 is a photograph of an sodium dodecyl sulfate—polyacrylamide gel electrophoresis (SDS-PAGE) gel following analysis of recombinant A-SAA2 expressed from pGEX as described in Example 2.

FIG. 1 illustrates the expression of the recombinant A-SAA2 protein from pGEX(A-SAA2) analysed by SDS-PAGE.

Key to FIG. 1:
Lane 1: protein molecular weight markers 55.6, 39.2, 26.6, 12.5, 6.5 kDa;
Lane 2: pGEX(A-SAA2) uninduced;
Lane 3: pGEX-2T expression vector induced with IPTG;
Lane 4: pGEX(A-SAA2) induced with IPTG;
Lane 5: thrombin cleaved mature A-SAA2 product; and
Lane 6: purified recombinant A-SAA2 following ion-exchange chromatography.

Cell pellets were resuspended in 1/50 of the starting volume in lysis buffer [phosphate buffered saline (PBS) pH 7.3 (Gibco/BRL, Paisley, U.K.) containing 0.2 mg/ml lysozyme (Sigma); 5 mM ethylenediaminetetraacetic acid (EDTA) (BDH, Merck, Dorset, England); 0.1% (v/v) TRITON X-100 (nonionic surfactants) (BDH); 50 mM benzamidine (Sigma); 0.1 mM phenylmethylsulfonyl fluoride (PMSF) (Sigma) and 0.5 mg/ml iodoacetamide (Sigma)] and incubated for 1 h at room temperature. Solubilisation of GST-(A-SAA2) from lysed E.coli cell pellets requires the presence of 0.1% (v/v) TRITON X-100 (see FIG. 2).

Recombinant GST-(A-SAA2) fusion protein was tested for solubility in the presence and absence of nonionic detergent 0.1% (v/v) TRITON X-100 followed by SDS-PAGE analysis. The results are depicted in FIG. 2.

Figure 2:
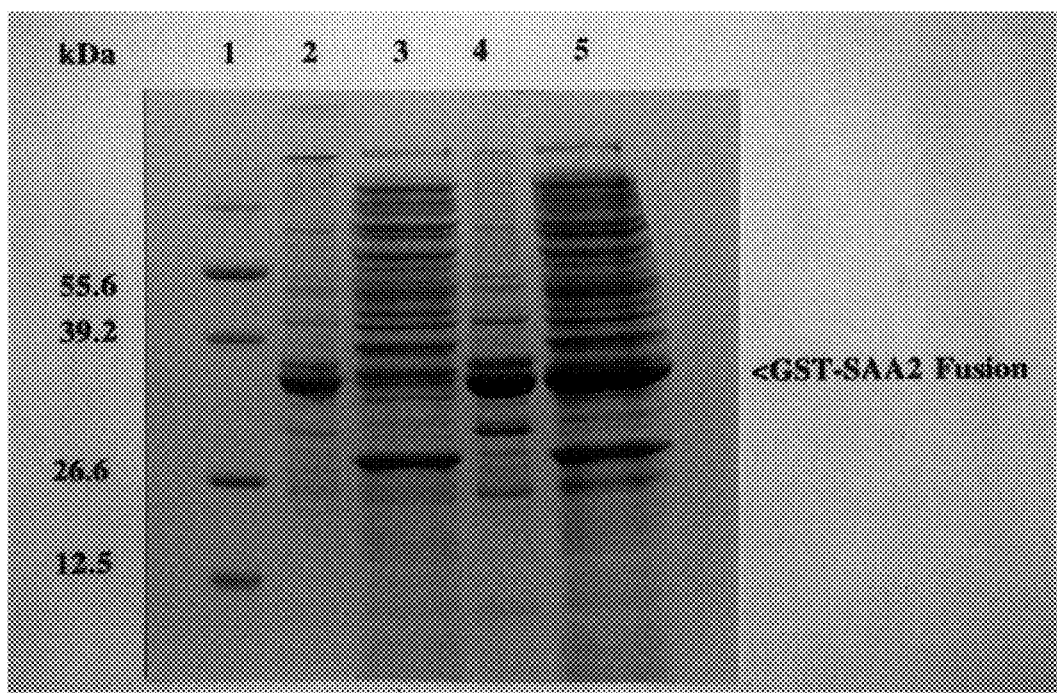
FIG. 2 is a photograph of an SDS-PAGE gel following analysis of extracted recombinant GST-(A-SAA2) fusion protein as described in Example 2.

Key to FIG. 2:
Lane 1: protein molecular weight markers 55.6, 39.2, 26.6, 12.5 kDa;
Lane 2; Insoluble fraction after cell lysis without the presence of 0.1% (v/v) TRITON X-100;
Lane 3: Soluble fraction without the presence of 0.1% (v/v) TRITON X-100;
Lane 4; Insoluble fraction after cell lysis in the presence of 0.1% (v/v) TRITON X-100; and
Lane 5: Soluble fraction in presence of 0.1% (v/v) TRITON X-100.

Lysates were sonicated on ice (3×20 second bursts) to obtain complete lysis, centrifuged at 10000×g for 10 min at 4° C. and filtered through a 0.45 μM MILLIPORE filter to remove particulate material. Clarified sonicates were passed through a Glutathione SEPHAROSE 4B column (agarose gel based column) (Pharmacia) to which the GST-(A-SAA2) fusion protein bound. Contaminating E. coli proteins were removed by washing with ten column volumes of PBS (pH 7.3), and the recombinant A-SAA2 protein was directly cleaved from the GST moiety on the Glutathione SEPHAROSE 4B column using thrombin (Sigma) (5 U/mg protein bound) in PBS (pH 7.3) 0.1% (v/v) TRITON X-100 at room temperature for 6 h. Cleavage by thrombin in the presence of 0.1% (v/v) TRITON X-100 yielded a soluble A-SAA2 product of 12.5 kDa [the predicted size for mature A-SAA2] (see FIGS. 1 (cleaved) and 2 (uncleaved), lane 5). The column eluate containing recombinant A-SAA2 was collected and stored at 4° C. The recombinant A-SAA2 sample was further purified by ion exchange chromatography using a column of high performance SEPHAROSE Q (agarose based ion exchange column) (Pharmacia) equilibrated with 0.1% (v/v) TRITON X-100, 20 mM Tris-HCl (pH 10.0) and eluted with 0.1% (v/v) TRITON X-100, 20 mM Tris-HCl (pH 10.0), 0.1 M NaCl. Fractions were collected and analysed by SDS-PAGE.

Further purification of recombinant A-SAA2 was achieved using ion exchange chromatography and the resulting protein could be resolved as a single band on SDS-PAGE (FIG. 1, lane 6). N-terminal amino acid sequence of the 12.5 kDa product was Gly-Ser-Gly-Arg-Ser-Phe-Phe-Ser-Phe-Leu-Gly-Glu-Ala-Phe-Asp-Gly-Ala-Arg-Asp (SEQ ID NO.3), confirming its identity as A-SAA2 with an amino terminal Gly-Ser-Gly extension derived from the fusion protein. The N-terminal sequencing of recombinant A-SAA2 was carried out by electroblotting the recombinant A-SAA2 onto a PROBOLTT membrane and staining with amido black prior to N-terminal amino acid sequencing on a BIOSYSTEMS model 473A protein sequencer. Approximately 3 mg of recombinant A-SAA2 was obtained per liter of bacterial culture.

Fractions following purification on the affinity column were also analysed by immunoblotting. For the SDS-PAGE and the immunoblotting anti(A-SAA) antiserum (see Example 3) was used with peroxidase-conjugated goat anti-rabbit IgG (Sigma) as the secondary antibody. The protein content of the fractions was determined using bicinchoninic acid solution (Sigma) with crystalline bovine serum albumin (BSA) (Sigma) as standard. Recombinant A-SAA2 was stored at 4° C. in buffer A (20 mM Tris-HCl (pH 8.4), 150 mM NaCl and 0.1% (v/v) TRITON X-100).

EXAMPLE 3

Antibodies to A-SAA2

Rabbits were immunised intramuscularly with recombinant A-SAA2 purified from SDS-PAGE gels prepared in Example 2, according to the method of (Hager, D. A. and Burgess, R. R. et al. (1980); Anal. Biochem. 109, 76) as follows: Day 1, 1 ml of 1 mg/ml recombinant A-SAA2 in Freunds complete adjuvant (Sigma); Days 14 and 21, 1 ml of 1 mg/ml recombinant A-SAA2 in Freunds incomplete adjuvant (Sigma). Blood was drawn on Day 28. IgG-anti (A-SAA) was isolated by affinity chromatography on immobilised Protein A (Pharmacia). The resulting antiserum was tested for cross-reactivity with other human SAA protein family members and serum components by immunoblot analysis (see FIG. 3).

Figure 3:
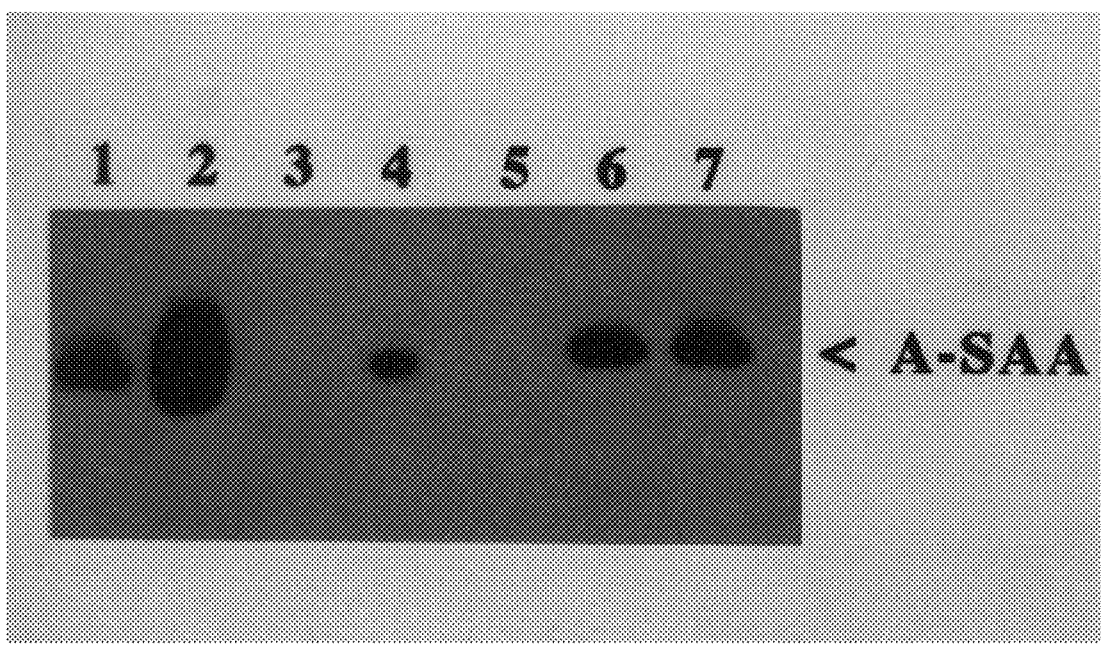
FIG. 3 is a photograph of an immunoblot following analysis of antiserum raised against recombinant A-SAA2 when tested for reactivity against recombinant and native A-SAA and potential cross-reactivity versus C-SAA as described in Example 3.

Key to FIG. 3:
Lane 1: recombinant A-SAA2;
Lane 2: Serum of an acute phase patient;
Lane 3: Non-acute phase serum;
Lane 4: NIBSC (National Institute of Biological Standards and Controls) A-SAA;
Lane 5: recombinant C-SAA;
Lane 6: recombinant A-SAA1; and
Lane 7: recombinant A-SAA2 spiked into non-acute phase serum.

The antiserum reacted with (i) purified recombinant A-SAA2 (FIG. 3, lane 1); (ii) A-SAA (but no other molecular species) present in the serum of a patient with inflammation (FIG. 3, lane 2) and A-SAA obtained from the NIBSC (FIG. 3, lane 4); (iii) recombinant A-SAA2 spiked into non-acute phase serum (FIG. 3, lane 7) and (iv) recombinant A-SAA1 [expressed and purified as for A-SAA2] (FIG. 3, lane 6). Antibodies raised against recombinant A-SAA2 generate equivalent signals with both recombinant A-SAA1 and recombinant A-SAA2 in the immunoblot (compare lanes 1 and 6 of FIG. 3) indicating that the binding capacity for each isoform is essentially equivalent. In addition, the antibodies raised against recombinant A-SAA2 did not cross react with purified C-SAA [expressed and purified as for A-SAA2] (FIG. 3, lane 5) or any component of non-acute phase serum (FIG. 3, lane 3).

EXAMPLE 4

An ELISA procedure in accordance with the invention involves coating of microtitre plates with purified IgG[anti-A-SAA] obtained as described in Example 3 and performance of the assay procedure:

1. Coating of Microtitre Plates

Microtitre maxisorp plates (Nunc, Denmark) were coated with affinity purified IgG[antiSAA2] (1.0 $\mu$g/ml in 0.1 M carbonate buffer, pH 9.6) overnight at 4° C. Plates were washed twice with PBS containing TWEEN-20 nonionic detergent 0.05% (PBST), and a BSA-containing blocking buffer was added to the wells.

Microtitre plates were incubated for 1 hour at 37° C. The blocking buffer was removed and the plates were dried overnight at 37° C. The microtitre plates were sealed and stored at 4° C. until required.

2. Assay Procedure (a) Serum samples and assay calibrator (recombinant A-SAA) were diluted in the sample dilution buffer:
20 mM Tris-HCl pH 7.8
150 mM NaCl
25% (v/v) propan-2-ol
and 100 $\mu$ of each dilution were added in duplicate to the microwells. After incubation at room temperature (20–25° C.) for 60 minutes with uniform shaking, wells were washed four times with 350 $\mu$l PBST using a plate washer.

(b) Enzyme conjugate (IgG[anti-SAA2]-horseradish peroxidase (HRP) was diluted in conjugate dilution buffer (50 mM TrisHCl pH 7.8, 150 mM NaCl, 1% (w/v) BSA) and 100 $\mu$l aliquots were added to the wells. The enzyme conjugate was produced essentially as described by Duncan, R. J. S. et al. (1983); Anal. Biochem. 132, 68. HRP was obtained from Biozyme Ltd., UK. Microtitre plates were incubated at room temperature (20–25° C.) for a further 60 minutes with uniform shaking. The wells were washed four times with 350 $\mu$l PBST.

(c) 100 $\mu$l of stabilised tetramethylbenzidene (TMB) substrate was added to each well using a multichannel pipette, and plates were incubated at room temperature for 15 minutes. Colour development was stopped using 100 $\mu$l IN $H_2SO_4$ and plates were read immediately at O.D.450 nm on a plate reader.

Figure 4:
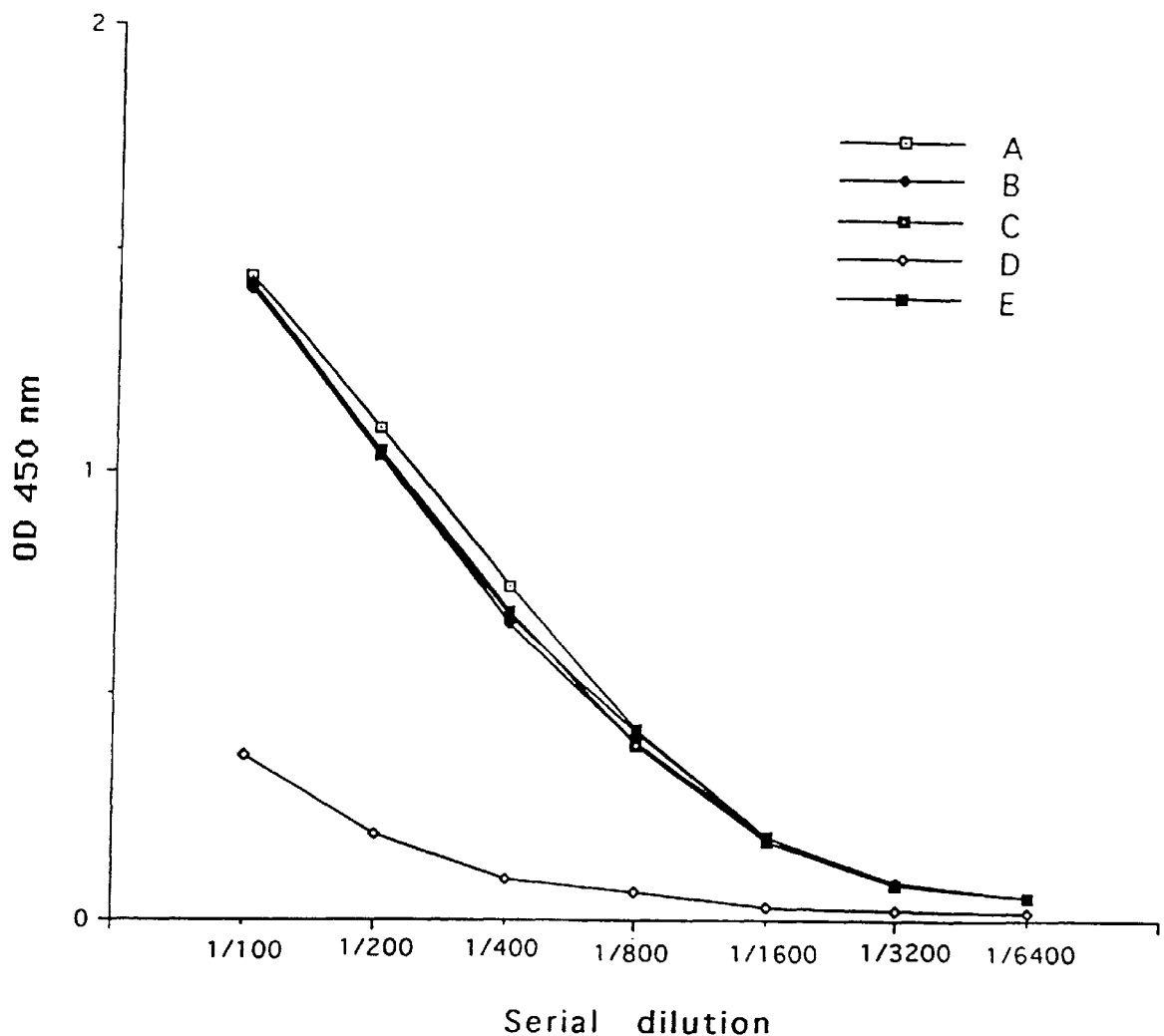
FIG. 4 is a standard curve for A-SAA for the assay described in Example 4.

(d) Standard Curve for A-SAA: Native SAA obtained from the National Institute of Biological Standards and Controls (NIBSC, UK) and recombinant SAA2 protein were both used to generate standard curves. Results were identical in both cases. The A-SAA standard curve range of 5–750 $\mu$g/L is prepared in sample dilution buffer as described above (20 mM Tris-HCl pH 7.8, 150 mM NaCl, 25% (v/v) propan-2 ol). Each of the specified parameters of temperature, time, and concentration may be varied in accordance with standard laboratory practise without substantially affecting the utility of the procedure. The standard curve obtained using the SAA standards was used to calculate the SAA concentration in the test samples (FIG. 4).

EXAMPLE 5

Figure 5:
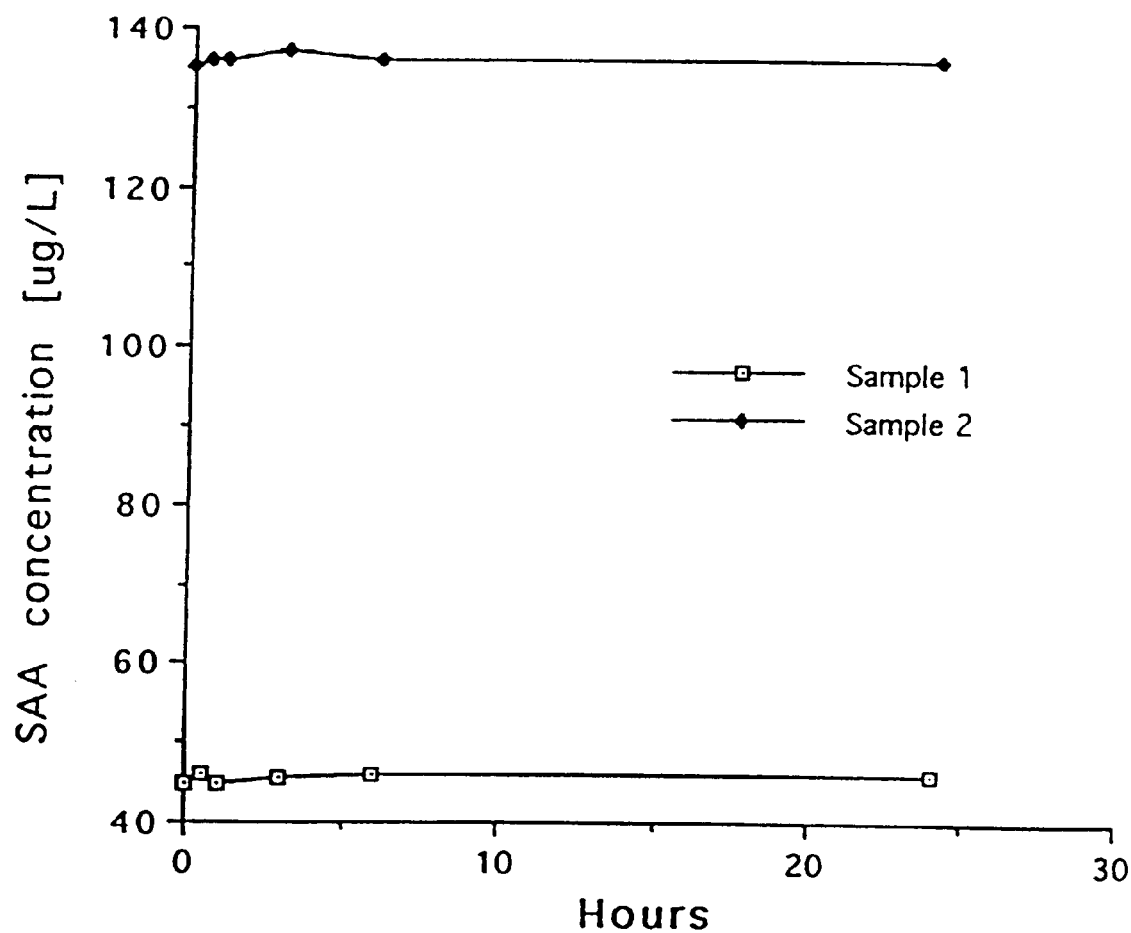
FIG. 5 is a graph of SAA concentration (µg/L) versus time (hours) for two samples as described in Example 5.
Figure 6:
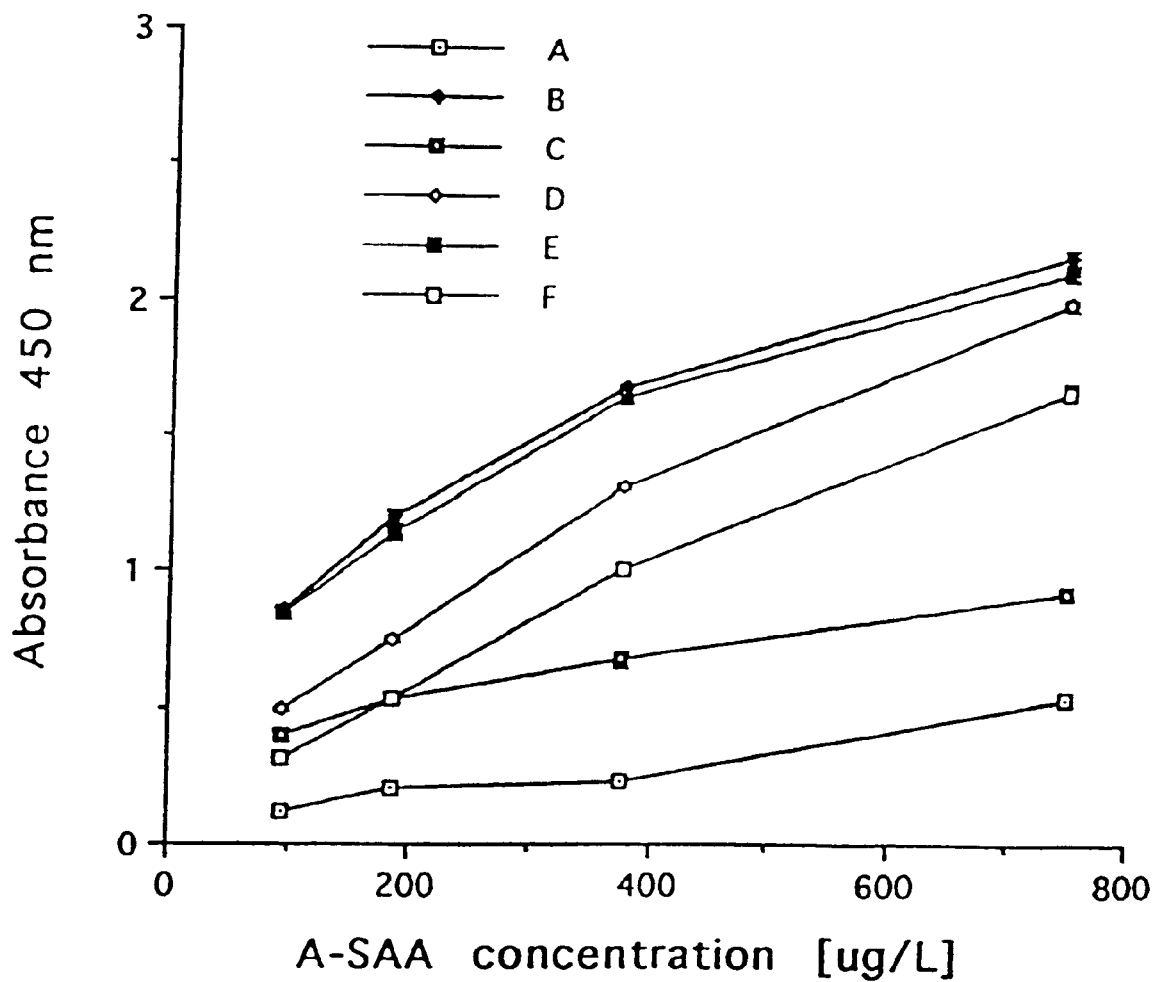
FIG. 6 is a graph of absorbance at 450 nm versus A-SAA concentration (µg/L) for various concentrations of an organic solvent in a sample dilution buffer as described in Example 6.

The use of propan-2-ol in the sample dilution buffer was tested for suitability as a routine reagent. Samples were diluted in propan-2-ol dilution buffer and left at room temperature for a period of 24 hours. The samples were assayed at different time points; immediately after dilution and subsequently at 0.5 hour, 1 hour, 3 hours, 6 hours and 24 hours, to investgate if any change in immunoreactivity occurred when samples were left in the organic sample dilution buffer. No variability of signal return was observed for the different serum samples indicating that there is no degradation of A-SAA epitopes and that the propan-2-ol dilution buffer can be used routinely in clinical investigations. The results are depicted in FIG. 5.

EXAMPLE 6

Masking Effect

Spiking experiments to investigate if any serum proteins interfere with A-SAA quantitation were carried out. In these experiments we examined if we could recover the same amount of A-SAA following the spiking of known amounts of recombinant A-SAA into non-acute phase serum. While 100% detection was observed when the recombinant A-SAA was spiked into sample dilution buffer, only 26% detection was obtained following the spiking of recombinant SAA2 into non-acute phase serum as shown in Table 1.

TABLE 1

The % recovery using the ELISA following spiking of recombinant A-SAA into non-acute phase serum.

| Dilution buffer | recombinant A-SAA2 $\mu$g/L spiked | recombinant A-SAA2 $\mu$g/L recovered | % recovery |
| --- | --- | --- | --- |
| — | 750 | 190 | 26 |
|   | 375 | 120 | 32 |
|   | 188 | 40  | 21 |

This shows that certain serum components mask the SAA signal. Tino-Casl & Grubb (1993) also observed masking of the SAA signal and theorised that IgG and HDL were the dominant proteins in the masking fractions. They proposed that there was no detectable masking of the antigen signal in their ELISA procedure if samples were prediluted 1:500 prior to assay and a final concentration of 0.2% (v/v) normal serum was present in their dilution buffer. However no spiking experiments to examine the absolute level of initial or residual masking were reported in their study. In our assay system, 0.2% serum in the dilution buffer did not reduce the masking effect to any great extent (data not shown). A variety of buffers containing various reagents such as TWEEN 20, TRITON X-100, NONIDET P-40, SDS, urea did not reduce or eliminate the masking effect on the SAA signal as shown in Table 2.

TABLE 2

The ELISA was used to investigate if different detergents/denaturants in the sample dilution buffer could increase the recovery of spiked recombinant A-SAA in nonacute phase serum.

| Dilution buffer | recombinant A-SAA2 µg/L spiked | recombinant A-SAA2 µg/L recovered | % recovery |
| --- | --- | --- | --- |
|  | 750 | 190 | 26 |
| 2M Urea | 750 | 188 | 25 |
| 6M Urea | 750 | 210 | 28 |
| 8M Urea | 750 | 190 | 26 |
| 1% TRITON | 750 | 180 | 24 |
| 1% TRITON + 1% BSA | 750 | 150 | 20 |
| 1% TWEEN | 750 | 202 | 27 |
| 1% TWEEN + 1% BSA | 750 | 202 | 27 |
| 1% SDS | 750 | 210 | 28 |
| 1% SDS + 1% BSA | 750 | 190 | 26 |
| 1% NP40 | 750 | 173 | 23 |
| 1% NP40 + 1% BSA | 750 | 158 | 21 |

It was observed that the presence of propan-2-ol at a concentration of 25%(v/v) as well as other alcohols\organic solvents in the sample dilution buffer led to the complete quantitative recovery of the A-SAA signal following spiking of non-acute phase serum with recombinant A-SAA as shown in Table 3 and FIG. 5.

TABLE 3

The ELISA was used to investigate if different organic solvents in the sample dilution buffer could increase the recovery of spiked recombinant A-SAA2 in non-acute phase serum.

| Dilution buffer | recombinant A-SAA2 µg/L spiked | recombinant A-SAA2 µg/L recovered | % recovery |
| --- | --- | --- | --- |
| No organic solvent | 750 | 190 | 26 |
| 25% Propan-2-ol | 750 | 733 | 98 |
| 25% Methanol | 750 | 713 | 95 |
| 25% Ethanol | 750 | 720 | 96 |
| 25% Ethanol/Ether 3:1 | 750 | 730 | 97 |

FIG. 5: FIG. 5 depicts the results of an investigation of the unmasking capacity of various concentrations of propan-2-ol in the sample dilution buffer. Recombinant A-SAA was spiked into non-acute phase serum and assayed in dilution buffer containing no propan-2-ol.

Key to FIG. 5:
(A) Recombinant A-SAA2 was spiked into buffer A and assayed in dilution buffer containing no propan-2-ol
(B) Recombinant A-SAA2- was spiked into non acute phase serum and assayed in dilution buffer containing:
(C) 10% propan-2-ol;
(D) 20% propan-2-ol;
(E) 25% propan-2-ol; and
(F) 40% propan-2-ol.

It was also observed that the presence of 25%(v/v) propan-2-ol in the dilution buffer when preparing the native SAA standard (NIBSC) increased the signal obtained, thus demonstrating that purified native SAA spiked into serum is also subject to masking by serum components as shown in Example 7.

EXAMPLE 7

Comparative Data

Comparison between recombinant SAA2 and serum samples containing an identical amount of acute phase SAA is essential to ensure that the IgG [anti-SAA2 (recombinant)] recognises both types in a similar manner. As can be seen from Table 4, this is indeed the case whereby IgG raised against the recombinant SAA2 reacts identically with acute phase SAA purified from human serum.

TABLE 4

Comparative reactivity between recombinant and native SAA with IgG raised against the recombinant form of SAA2.

| [SAA] (µg/L) | $A_{450/630}$ nm Recombinant SAA2 | Native SAA |
| --- | --- | --- |
| 1500 | 1.492 | 1.217 |
| 750 | 0.807 | 0.915 |
| 325 | 0.467 | 0.604 |
| 187 | 0.213 | 0.311 |
| 94 | 0.086 | 0.139 |
| 46 | 0.046 | 0.087 |
| 23 | 0.033 | 0.043 |
| 0 | 0.006 | 0.000 |

EXAMPLE 8

Clinical Utility

The upper limit of normal for acute phase SAA in serum is known to be less than 10 mg/L. Using the immunoassay described in Example 4, no detectable amounts of acute phase SAA were detectable in many normal human serum samples and less than 10 mg/L was detectable in SAA are elevated in the case of both rheumatoid arthritis and acute pancreatitis, respectively as measured by the enzyme immunoassay.

TABLE 5

SAA levels in diseases states as measured by the enzyme immunoassay.

| Disease State | [SAA] (mg/L, mean ± SD) | n |
| --- | --- | --- |
| Rheumatoid Arthritis | 92.4 ± 150 | 19 |
| Acute Pancreatitis | 309 ± 140 | 15 |

EXAMPLE 9

Some previous reports of methods to measure A-SAA in patient serum have identified problems associated with quenching of the A-SAA signal by serum components (Casl et al., 1993). To address this issue, we conducted experiments in which purified recombinant A-SAA2 was added to serum (spiked) and interference caused by serum components was quantified. Recombinant A-SAA2 at a known concentration was spiked into (i) buffer A and (ii) non acute phase serum, and assayed using the sample dilution buffer without 25% (v/v) propan-2-ol. Only 26% recovery of signal was observed following the spiking of recombinant A-SAA2 into non-acute phase serum as shown in Table 1.

The above spiking experiment was repeated using sample dilution buffer containing 25% (v/v) propan-2-ol. In the presence of the organic solvent almost complete recovery of signal was observed following spiking of recombinant A-SAA2 into non-acute phase serum (Table 6).

TABLE 6

Spiking of recombinant A-SAA2 into non-acute phase serum. Serial dilutions were carried out in dilution buffer with 25% (v/v) propan-2-ol.

| Dilution buffer with 25 % (v/v) propan-2-ol | recombinant A-SAA2 µg/L spiked | recombinant A-SAA2 µg/L recovered | % recovery |
|---|---|---|---|
| | 750 | 740 | 98 |
| | 375 | 358 | 95 |
| | 188 | 178 | 95 |

Figure 7:
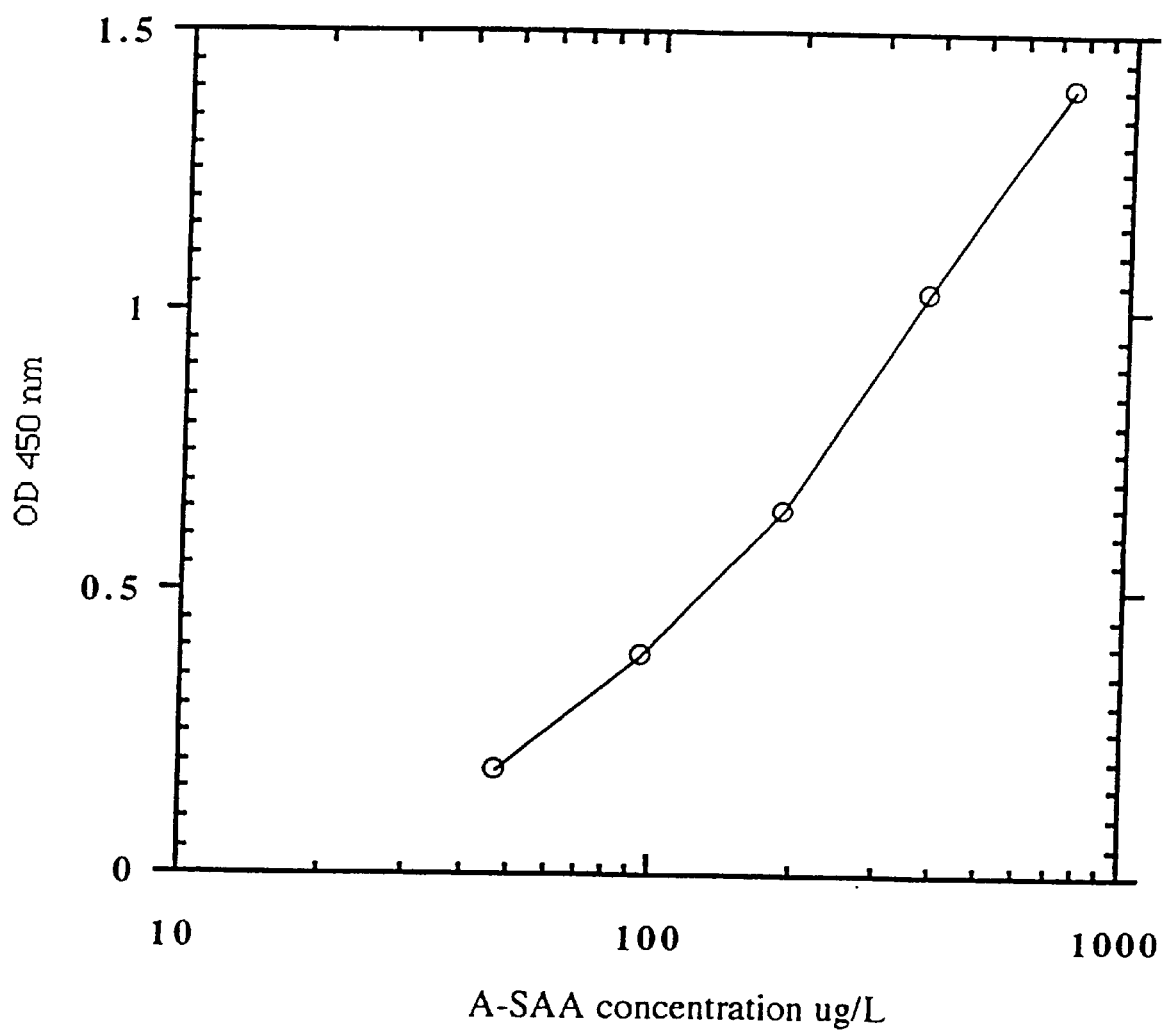
FIG. 7 is a graph of optical density (absorbance) at 450 nm versus serial dilution for various samples as described in Example 9.

Although not wishing to be bound by any theoretical explanation of the invention, the propan-2-ol sample dilution buffer most likely achieves signal recovery by disrupting the hydrophobic apolipoprotein complexes thereby facilitating antibody access to otherwise hidden A-SAA epitopes. From our studies purified recombinant with A-SAA2 in buffer A, A-SAA2 spiked into non-acute phase serum, and native A-SAA in serum from a rheumatoid arthritis patient, all show similar serial dilution profiles when diluted in our sample dilution buffer (FIG. 7). The presence of propan-2-ol in the sample dilution buffer offers a simple, rapid alternative to previous methods used to unmask the A-SAA in serum samples prior to immobilisation on.solid phases.

EXAMPLE 10

Serum Samples

As in further exemplification of the clinical data of Example 8, normal serum samples were obtained from blood donors aged 18–65 years. Rheumatoid arthritis serum samples were obtained from patients undergoing routine assessment in the Rheumatology Clinic of St James Hospital, Dublin. Samples were stored at −20° C. prior to use. patients undergoing routine assessment in the Rheumatology Clinic of St James Hospital, Dublin. Samples were stored at −20° C. prior to use.

In the A-SAA sandwich ELISA serum samples were routinely run at 1/200 dilution. The lower and upper limits of the low range standard curve were 5 µg/L and 100 µg/L respectively. The lower and upper limits of the high range standard curve were 50 µg/L and 750 µg/L, respectively (FIG. 4), and samples falling above this range were diluted appropriately so that their A-SAA levels fell within the range of the curve. For assay validation the linearity of sample dilution was analysed by carrying out serial dilutions and the resulting data show that assay parallelism is observed in the ELISA. The reproducibility of the ELISA method was analysed by intra-assay and inter-assay variability. The intra-assay coefficient of variation from twenty replicate assays of three A-SAA serum samples (A-SAA concentrations were 5, 130 and 244 mg/L) were 4.8, 5.0 and 6.7%, respectively. The inter-assay coefficient of variation in ten replicate assays on the same serum samples were 8.0, 6.2 and 6.0%, respectively.

Figure 8:
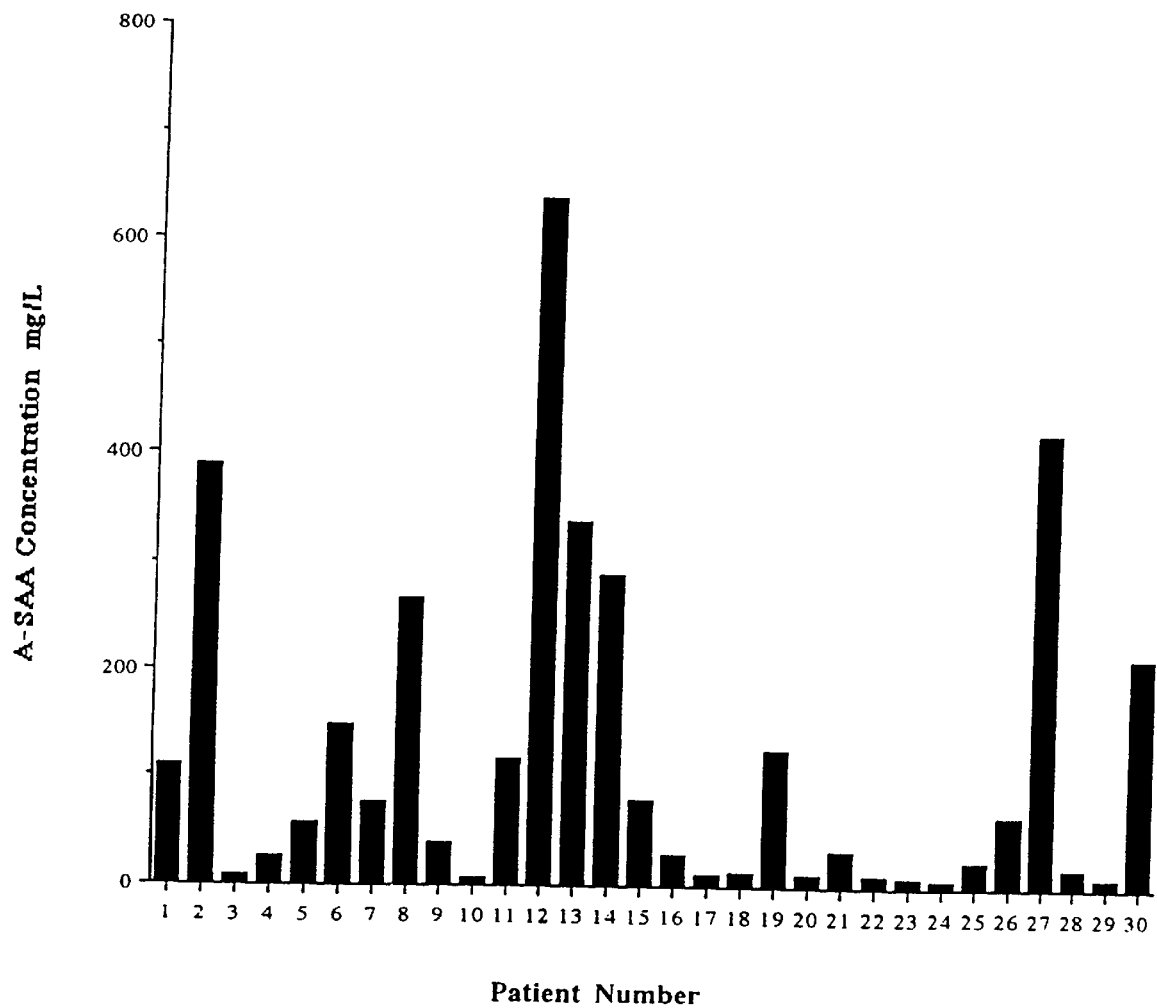
FIG. 8 is a bar graph representation of A-SAA concentration in the serum of rheumatoid arthritis patients as described in Example 10.

The normal range for A-SAA was analysed using 50 serum samples from healthy individuals, and determined to be 0.4 mg/L ±0.57 mg/L using the standard equation: mean ±2 SD. The A-SAA concentrations in 30 serum samples from rheumatoid arthritis patients were analysed using the ELISA procedure of Example 4 and 95% of rheumatoid arthritis patients showed an elevated level of A-SAA (FIG. 8).

A-SAA proteins are difficult to isolate, purify and solubilise. The production of A-SAA2 by thrombin cleavage from a GST-(A-SAA2) fusion protein in conjunction with the use of TRITON X-100 for solubilisation offers a means of generating large amounts of homogeneous A-SAA. As the recovery of soluble A-SAA2 by this method is possible without the use of harsh denaturants the resulting material may be particularly suited to future studies of A-SAA structure and biological function. Antibodies generated against recombinant A-SAA2 were shown to be specific for A-SAAs and used to develop an ELISA for quantifying A-SAA in patient serum as hereinbefore exemplified. Monitoring acute phase protein levels is of considerable clinical importance in the assessment of inflammatory disease activity and response to therapy and the ELISA reported here provides a simple, rapid and reproducible method for such monitoring.

What is claimed is:

1. A method for quantitatively determining human acute phase serum amyloid A protein (A-SAA), A-SAA1 and/or A-SAA2, which comprises
   a) contacting a sample of a biological fluid with antibody specific for the A-SAA (anti-A-SAA), wherein the anti-A-SAA is raised against recombinant A-SAA which is free from C-SAA and which is soluble under physiological conditions;
   b) contacting said sample with an organic solvent in an amount sufficient to unmask A-SAA epitopes prior to or simultaneous with the anti-A-SAA antibody contact; and
   c) determining the amount of the A-SAA present in the sample.

2. The method according to claim 1, wherein the biological fluid is plasma or serum.

3. The method according to claim 1, wherein the antigen used to raise the anti-A-SAA is recombinant A-SAA2.

4. The method according to claim 1, wherein the organic solvent is a polar organic solvent.

5. The method according to claim 4, wherein the organic solvent comprises a $C_1$–$C_4$ alcohol.

6. The method according to claim 5, wherein the organic solvent further comprises a $C_1$–$C_4$ ether.

7. A method according to claim 1, wherein the organic solvent is used in an amount of 10–50% v/v of a sample diluent.

8. The method according to claim 7, wherein the organic solvent is used in an amount of 20–30% v/v of the sample diluent.

9. The method according to claim 1, wherein the anti-A-SAA antibody is linked to a solid phase as a component of a detection system of an enzyme linked immunosorbant assay.

10. A test kit or pack for quantitatively determining human A-SAA in a biological sample by contacting said sample with an A-SAA specific antibody and an organic solvent present in an amount sufficient to unmask A-SAA epitopes, comprising:
    an antibody specific for A-SAA; and
    an organic solvent.

11. Recombinant human A-SAA2, which is free from human A-SAA1 and C-SAA and which is soluble under physiological conditions.

12. Purified antibody specific for A-SAA1 and A-SAA2.

13. The recombinant human A-SAA2 of claim 11, which is free from human A-SAA1 and C-SAA and which can be used to raise A-SAA specific antibodies.

14. Purified recombinant human A-SAA2 of claim 11, which is free from human A-SAA1 and C-SAA and which can be used to raise A-SAA specific antibodies.

* * * * *